US010744088B2

(12) United States Patent
Lee et al.

(10) Patent No.: US 10,744,088 B2
(45) Date of Patent: Aug. 18, 2020

(54) METHOD FOR PREPARING OPHTHALMIC PREPARATION CONTAINING THYMOSIN BETA-4

(71) Applicant: G-TREEBNT CO., LTD., Seongnam-si, Gyeonggi-do (KR)

(72) Inventors: Si Young Lee, Ansan-si (KR); Sin Wook Kang, Seongnam-si (KR); Ji Hye Sung, Seoul (KR); Tae Heum Um, Seoul (KR)

(73) Assignee: G-TREEBNT CO., LTD., Seongnam-si (KR)

( * ) Notice: Subject to any disclaimer, the term of this patent is extended or adjusted under 35 U.S.C. 154(b) by 0 days.

(21) Appl. No.: 15/752,118

(22) PCT Filed: Dec. 18, 2015

(86) PCT No.: PCT/KR2015/013981
§ 371 (c)(1),
(2) Date: Feb. 12, 2018

(87) PCT Pub. No.: WO2017/061663
PCT Pub. Date: Apr. 13, 2017

(65) Prior Publication Data
US 2018/0228729 A1 Aug. 16, 2018

(30) Foreign Application Priority Data
Oct. 6, 2015 (KR) .................... 10-2015-0140489

(51) Int. Cl.
| | |
|---|---|
| *A61K 38/22* | (2006.01) |
| *A61K 9/08* | (2006.01) |
| *C01B 23/00* | (2006.01) |
| *A61J 1/14* | (2006.01) |
| *A61K 9/00* | (2006.01) |
| *A61K 47/02* | (2006.01) |
| *A61J 1/12* | (2006.01) |

(52) U.S. Cl.
CPC ............ *A61K 9/08* (2013.01); *A61J 1/1468* (2015.05); *A61K 9/0048* (2013.01); *A61K 38/22* (2013.01); *A61K 38/2292* (2013.01); *A61K 47/02* (2013.01); *C01B 23/00* (2013.01); *A61J 1/12* (2013.01)

(58) Field of Classification Search
None
See application file for complete search history.

(56) References Cited

U.S. PATENT DOCUMENTS

| | | | | |
|---|---|---|---|---|
| 4,150,744 | A * | 4/1979 | Fennimore | A61J 1/16 206/205 |
| 6,271,216 | B1 * | 8/2001 | Mello | A61K 9/0048 424/678 |
| 8,143,218 | B2 | 3/2012 | Kleinman et al. | |
| 2008/0302830 | A1 * | 12/2008 | Loth-Krausser | A61F 9/0008 222/215 |
| 2012/0071411 | A1 * | 3/2012 | Crockford | A61K 9/0048 514/12.9 |
| 2013/0172529 | A1 * | 7/2013 | Fernandez Carneado | C07K 14/57581 530/324 |

FOREIGN PATENT DOCUMENTS

| | | |
|---|---|---|
| KR | 10-1998-0703582 A | 11/1998 |
| KR | 10-2001-0099686 A | 11/2001 |
| KR | 10-2006-0051135 A | 5/2006 |
| KR | 10-2008-0033939 A | 4/2008 |
| KR | 10-2015-0080026 A | 7/2015 |
| WO | 2008/108927 A2 | 9/2008 |
| WO | WO-2008108927 A2 * | 9/2008 ............ A61K 47/38 |

OTHER PUBLICATIONS

National Center for Biotechnology Information. PubChem Database. Sodium acetate hydrate, CID=23681166, https://pubchem.ncbi.nlm.nih.gov/compound/Sodium-acetate-hydrate (accessed on Mar. 13, 2020) (Year: 2020).*
National Center for Biotechnology Information. PubChem Database. Sodium acetate trihydrate, CID=23665404, https://pubchem.ncbi.nlm.nih.gov/compound/Sodium-acetate-trihydrate (accessed on Mar. 13, 2020) (Year: 2020).*
National Center for Biotechnology Information. PubChem Database. Calcium chloride hydrate, CID=16211463, https://pubchem.ncbi.nlm.nih.gov/compound/Calcium-chloride-hydrate (accessed on Mar. 13, 2020) (Year: 2020).*
National Center for Biotechnology Information. PubChem Database. Calcium chloride, dihydrate, CID=24844, https://pubchem.ncbi.nlm.nih.gov/compound/Calcium-chloride_-dihydrate (accessed on Mar. 13, 2020) (Year: 2020).*
Gabriel Sosne, et al., "Thymosin Beta 4 Promotes Corneal Wound Healing and Decreases Inflammation in Vivo Following Alkali Injury", Experimental Eye Research, 2002., pp. 293-299, vol. 74.
International Search Report for PCT/KR2015/013981 dated May 25, 2016 [PCT/ISA/210].
Extended European Search Report dated Feb. 14, 2019 in European Application No. 15905904.7.
Hannappel et al., "The Thymosins: Prothymosin α, Parathymosin, and β-Thymosins: Structure and Function", Vitamins and Hormones, Academic Press, vol. 66, pp. 257-296 (2003).

* cited by examiner

*Primary Examiner* — Lianko G Garyu
(74) *Attorney, Agent, or Firm* — Sughrue Mion, PLLC

(57) ABSTRACT

The present invention relates to a method for manufacturing an ophthalmic preparation comprising thymosin β4. According to the inventive method, the manufacture of an ophthalmic preparation comprising thymosin β4 is carried out in the presence of an inert gas, thus the contact of thymosin β4 with oxygen is blocked and the oxidation of thymosin β4 can be prevented and the pharmacological activity of thymosin β4 maintains for long-term period. Therefore, the ophthalmic preparation prepared by the inventive method can maintain the pharmacological activity of thymosin β4 in a stable state for a long time.

12 Claims, 2 Drawing Sheets

Specification includes a Sequence Listing.

METHOD FOR PREPARING OPHTHALMIC PREPARATION CONTAINING THYMOSIN BETA-4

CROSS REFERENCE TO RELATED APPLICATIONS

This application is a National Stage of International Application No. PCT/KR2015/013981, filed on Dec. 18, 2015, which claims priority from Korean Patent Application No. 10-2015-0140489, filed on Oct. 6, 2015, the contents of all of which are incorporated herein by reference in their entirety.

TECHNICAL FIELD

The present invention relates to a method for manufacturing an ophthalmic preparation containing thymosin β4.

BACKGROUND ART

The human eye is an organ of the body which is not reproducible. It is vulnerable to eye disorders such as degenerative diseases, glaucoma, or cataract in retina, cornea, conjunctiva or uvea. In particular, the cornea is a part of the outer membrane of the eyeball exposed to the outside. The cornea plays important roles in protecting the eyeball and transmitting light to the retina by refracting wavelengths entering into the eye. However, the cornea is vulnerable to injuries such as scratch or impact and so on since it does not have other protective structures except the eyelid. In addition, in case of serious damage to the cornea, there are no practical treatment options except transplantation. Unfortunately, however, it has been reported that the transplanted cornea exhibits poor biological adaptation and adverse events.

Recently, as more people are wearing contact lenses for vision correction or fashion, the number of people suffering from eye disorders such as corneal surface injury and dry eye syndrome, etc. is increasing. Since the cornea is overlaid with a contact lens, oxygen supply to the cornea is blocked and the dryness of the cornea gets worse by blocking the tear secreted at the lacrimal gland. As such, most of people wearing contact lenses frequently use artificial tears etc., to relieve the dryness of the cornea. If the dryness of the cornea get worse, the treatment of damaged cornea is essential for preventing progression to other eye disorders that can be triggered from it. Examples of treatments of corneal injury include direct application of ophthalmic drugs such as a liquid formulation, a gel or an ointment to the cornea.

Various forms of ophthalmic preparations are required to have an excellent pharmacological activity and maintain the activity through stable storage. The stability and pharmacological activity of the ophthalmic preparation are affected by its ingredient and content and the treatment conditions during manufacturing and distribution processes. Especially, in the whole manufacturing and distribution processes, the dehumidification and oxidation prevention of the ophthalmic preparation are very important. For this purpose, several methods to maintain the product quality are utilized including, for example, sealing packaging after sterilization; coloring a glass vial to prevent direct exposure to sunlight; and adding a dehumidifying agent such as a silica gel. However, even with the above various methods, it is still difficult to achieve quality maintenance depending on a seasonal temperature difference, a humidity change or oxidation. Thus, a need for an ophthalmic preparation having a good stability to maintain its pharmacological activity at a constant level is increasing.

Meanwhile, thymosin β4 is a protein discovered in the thymus in 1981, and consists of 41 to 43 amino acids, whose isoelectric point is 5.1. It was identified as an actin-sequestering molecule in animal cells by Riva in 1991, and then found to be involved in the immune regulation and neuroendocrine system. Moreover, it was found that thymosin β4 not only functions as a terminal deoxynucleotide transferase in thymocytes, but increases the migration of macrophages and its antigen and the secretion of luteinizing hormone by hypothalamic explants. It is also known to remove the toxicity of cytosine arabinoside and inhibit the cell cycle of hematopoietic stem cells to increase the adhesion and migration of endothelium.

Therefore, studies on the usage of thymosin β4 having the pharmacological activities as mentioned above for the treatment of ocular disorders were carried out. For example, Korean Laid-Open Patent Publication No. 10-2008-0033939 discloses a pharmaceutical composition to treat eye inflammations, eye infections (bacterial, fungal or viral), and glaucoma as uses of an ophthalmic solution comprising thymosin β4 and a preservative having sterilizing action. However, such pharmaceutical composition has the disadvantage that thymosin β4 that is prepared by a freeze-drying method and is labile to temperature change can be denatured depending on temperature change, which leads to the reduction of its pharmacological activity.

Korean Laid-Open Patent Publication No. 10-2015-0080026 discloses a preparation method comprising: adding a pH buffer and an antioxidant to an aqueous solution containing tetrahydrobiopterin (BH4) for oral administration, intravenous injection or co-administration with food; spraying a non-oxidizing gas thereto; and filling the aqueous solution into a container. However, since the aqueous solution containing BH4 as above is filled into a container in the presence of a non-oxidizing gas after it is prepared into a mixed solution containing BH4, a pH buffer, and an antioxidant etc. while being exposed to oxygen under the atmosphere before the filling process into container, it has the disadvantage that oxidation, addition of impurities and so on cannot be blocked during the above mixing step.

As such, the present inventors have endeavored to improve the stability of an ophthalmic preparation comprising thymosin β4 by blocking its modification, and to maintain its pharmacological activity at a constant level for long-term period, and found that stability of thymosin β4 and its ophthalmic preparation can be improved by blocking contact with oxygen using an inert gas during manufacturing and filling and sealing processes of the ophthalmic preparation.

DISCLOSURE OF INVENTION

Technical Problem

An object of the present invention is to provide a method for manufacturing an ophthalmic preparation comprising thymosin β4 with improved stability.

Solution to Problem

In accordance with above objective, the present invention provides a method for manufacturing an ophthalmic preparation comprising thymosin β4, which includes the steps of filling a composition comprising thymosin β4 into a container and sealing the container in the presence of an inert gas.

In accordance with above other objective, the present invention also provides an ophthalmic product prepared by the above manufacturing method.

Advantageous Effects of Invention

The manufacturing method of the present invention prevents oxidation of thymosin β4 and maintains its pharmacological activity for long-time period by manufacturing an ophthalmic preparation comprising thymosin β4 in the presence of an inert gas and thereby blocking the contact of thymosin β4 with oxygen. Therefore, the ophthalmic preparation prepared by manufacturing method of the present invention can maintain the pharmacological activity of thymosin β4 in a stable state for long-term period.

BEST MODE FOR CARRYING OUT THE INVENTION

Figure 1:
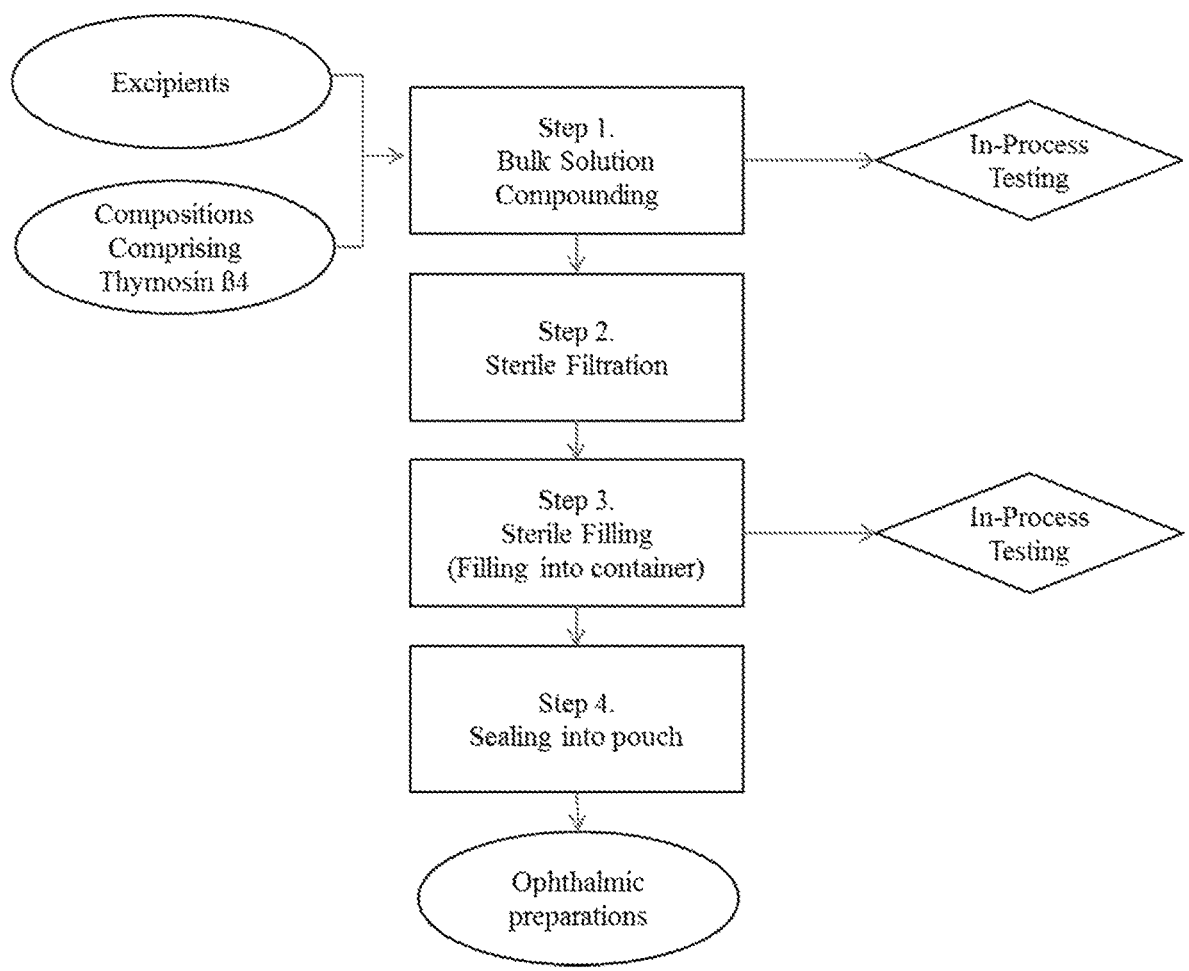
FIG. 1 is a schematic figure showing a method for manufacturing an ophthalmic preparation comprising thymosin β4.

The present invention provides a method for manufacturing an ophthalmic preparation comprising thymosin β4, which includes the steps of filling a composition comprising thymosin β4 into a container and sealing the container in the presence of an inert gas.

The term "thymosin β4", as used herein, refers to a protein called "Thymosin beta-4" or "Tβ4", which was first isolated in the thymus gland. It is a polypeptide composed of 43 amino acids of 4.9 kDa identified in various tissues. It is up-regulated during the migration and differentiation of endothelial cells in vitro. Various isoforms of thymosin β4 have been identified and they have about 70%, or about 75%, or about 80% or higher homology with the amino acid sequence of thymosin β4 publicly known. The thymosin β4 of the present invention may be N-terminal variants of wild type thymosin β4 or C-terminal variants of Tβ4. Specifically, it refers to a protein having the amino acid sequence represented by SEQ ID NO: 1.

The composition comprising thymosin β4 may be filled into a container and sealed in the presence of nitrogen or argon, specifically a nitrogen gas. An inert gas may also be filled and sealed together in order to prevent concomitant inflow of oxygen in container when filling and sealing. Examples of the inert gas may include helium, neon etc. in addition to nitrogen and argon. However, considering the cost, nitrogen and argon which are relatively cheap are mostly used, and specifically, nitrogen is mostly used.

Since the above inert gas is stable compared to oxygen or hydrogen molecules, the oxidation of thymosin β4 can be prevented by blocking the contact of the composition with oxygen under the atmosphere when a composition comprising thymosin β4 is filled into a container and sealed in the presence of an inert gas. In addition, since an inert gas is filled together during the filling and sealing processes, and thereby oxygen does not exist in the container, it is possible to persistently prevent the oxidation of thymosin β4 and maintain the pharmacological activity thereof.

The container of the conventional materials can be used as the container for the filling and sealing of the medicinal preparations. Specifically, a glass container, a polypropylene container, and a low density polyethylene container can be used. More specifically, a low density polyethylene container can be used.

A method for manufacturing an ophthalmic preparation of the present invention can be carried out according to the following specific procedures.

First, a composition comprising thymosin β4 is prepared by mixing a solvent with thymosin β4 in the presence of inert gas.

More particularly, a solvent in which impurities have been eliminated such as purified water, pure water or sterile water for injection is mixed with thymosin β4 in the presence of an inert gas such as nitrogen or argon. Specifically, thymosin β4 is mixed while removing oxygen dissolved in the solvent by bubbling nitrogen into the solvent at the rate of speed of 100 ml/min to 140 ml/min. The amount of thymosin β4 in the mixed composition may range from 0.05% (w/v) to 0.5% (w/v) based on the total composition, which may be administered in a total daily dose of 0.08 ml to 2.0 ml. The composition may be administered once or several times per day, specifically 2 to 5 times per day.

The mixture may be added with pharmaceutically acceptable excipients. The excipients for use in the present invention may be conventional excipients that can be added when preparing a medicinal preparation, specifically, sodium chloride, potassium chloride, calcium chloride hydrate, magnesium chloride hexahydrate, sodium acetate hydrate, sodium citrate hydrate etc.

In addition, the pH of the composition is adjusted to 6.8 to 7.2 using an acid or a base. The acid may be selected from the group consisting of hydrochloric acid, acetic acid, and phosphoric acid etc., specifically, hydrochloric acid. The base may be selected from the group consisting of sodium hydroxide, potassium hydroxide, and sodium hydrogen carbonate etc., specifically, sodium hydroxide.

Next, the pH adjusted composition is filtrated through a filter. Impurities and bacteria, etc. can be eliminated by filtration with a filter, specifically a sterile filter having a pore size of 1.0 μm or less, more specifically 0.2 μm or less.

The ophthalmic preparation where the composition comprising the thymosin β4 prepared by the above preparation method was filled is sealed into a pouch in the presence of an inert gas. The filling and sealing processes can be conducted in the presence of nitrogen gas to prevent concomitant inflow of oxygen.

Specific method for manufacturing an ophthalmic preparation comprising the thymosin β4 is described in FIG. 1, where each step is carried out in the presence of an inert gas to prevent the contact of thymosin β4 with oxygen.

The present invention provides ophthalmic products comprising thymosin β4 prepared by the above manufacturing method. Since every process for manufacturing the ophthalmic preparation comprising thymosin β4 is carried out in the presence of an inert gas, to prevent the formation of an oxide or mixing of impurities in the ophthalmic preparation and to maintain the physiochemical properties at a constant level for a long time, the inventive ophthalmic product can maintain the pharmacological activity of thymosin β4 for a long-term period in a more stable state.

Mode for the Invention

Hereinafter, in order to more clearly understand the present invention, the present invention will be described in more details by the following examples. However, the examples of the present invention may include different variations or modifications and it is not construed that the scope of the present invention is limited within the scope of the following examples.

EXAMPLE 1

Manufacture of Ophthalmic Preparation Comprising Thymosin β4

Step 1: Preparation of Ophthalmic Composition Comprising Thymosin β4

630 g of sterile water for injection was put into a pressurizable stainless steel stirring tank, and then while cooling to 5° C., nitrogen gas was bubbled through a sparger submerged in the solution at a rate of about 120 ml/min to remove oxygen dissolved in the solution. 4.89 g of sodium chloride, 573 mg of potassium chloride, 366.72 mg of calcium chloride hydrate, 229 mg of magnesium chloride hexahydrate, 2.98 g of sodium acetate hydrate, and 1.30 g of sodium citrate hydrate were added into the cooled solution, and dissolved with stirring while keeping the temperature to 3 to 7° C. 764 mg (a corrected amount with purity and peptide contents) of thymosin β4 acetate (Bachem, USA, SEQ ID NO: 1) was added to the resulting solution, and was completely dissolved with stirring at 3° C. to 7° C. While dissolving each component and thymosin β4, nitrogen was continuously supplied to prevent the contact of thymosin β4 with oxygen. The resulting solution was added with sodium hydroxide and hydrochloric acid to adjust its pH to 7.0, and then added 82 g of sterile water for injection to adjust the concentration of thymosin β4 to 1 mg/ml. The resulting mixture was subjected to a sterile filtration using 0.2 μm polyethersulfone (PES) sterile filter (Product number: MCY4440EKVPH4, Pall Corporation) under nitrogen pressurization, to obtain a filtered solution.

Step 2: Filling and Sealing Steps of the Ophthalmic Composition

The filtered sterile solution obtained in Step 1 was put into low density polyethylene vials at 0.27 ml/vial, and sealed with nitrogen gas charging into the vial. Then, the vials were sealed in aluminum pouches under nitrogen back flush to prepare ophthalmic preparations. The prepared ophthalmic preparations were stored at 2° C. to 8° C.

COMPARATIVE EXAMPLE 1

Manufacture of Ophthalmic Preparation Comprising Thymosin β4 Excluding Inert Gas—(1)

An ophthalmic preparation was prepared in the same manner as in Example 1, except that Steps 1 and 2 of Example 1 were conducted under the atmosphere (in the presence of $O_2$) without using an inert gas.

COMPARATIVE EXAMPLE 2

Manufacture of Ophthalmic Preparation Comprising Thymosin β4 Excluding Inert Gas—(2)

An ophthalmic preparation was prepared in the same manner as in Example 1, except that Step 1 of Example 1 was conducted under the atmosphere (in the presence of $O_2$) without using an inert gas.

TEST EXAMPLE 1

Stability Confirmation of Composition Comprising Thymosin β4

(1) Purity Analysis

The purity changes of the ophthalmic preparations prepared in the above Examples and Comparative Examples were analyzed during the period from the initial time after preparation to 12 months later with a high performance liquid chromatography (HPLC), Agilent 1200 instrument under the conditions in Tables 1 and 2, and the results are shown in Table 3.

TABLE 1

| HPLC operating condition | Column | Waters Delta-Pak C18 5 μm (3.9 × 150 mm) |
|---|---|---|
| | Mobile phase | A: water containing 0.1% by volume of trifluoroacetic acid (TFA) |
| | | B: acetonitrile containing 0.1% by volume of trifluoroacetic acid (TFA) |
| | Flow rate | 1.0 ml/min |
| | Detection | UV 205 nm |
| | Column temperature | Room temperature |
| | Injection volume | Purity test: 10 μl, Impurity test: 100 μl |

TABLE 2

| Gradient condition over time (minutes) | A (volume %) | B (volume %) |
|---|---|---|
| 0.0 | 85 | 15 |
| 15.0 | 75 | 25 |
| 15.1 | 20 | 80 |
| 17.0 | 20 | 80 |
| 17.1 | 85 | 15 |

(2) Impurity Analysis

The amounts of impurities in the ophthalmic preparations prepared in the above Examples and Comparative Examples were analyzed as following, and the results are shown in Table 3.

Specifically, thymosin β4 sulfoxide was synthesized following the methods in the paper (*Eur. J. Biochem.* 223, 345-350 (1994), *Nature Medicine* 5(12), 1424 (1999)). Thymosin β4 sulfoxide is a substance modified from thymosin β4 by oxidation, which causes a change in its pharmacological activity compared to thymosin β4.

The molecular weight of the synthesized thymosin β4 sulfoxide was identified by mass analysis (LC/MS) using the MALDI-TOF MS instrument. The analyzed molecular weight was 4,978.5, which was consistent with the value in the document of 4,980±2.

Figure 2:
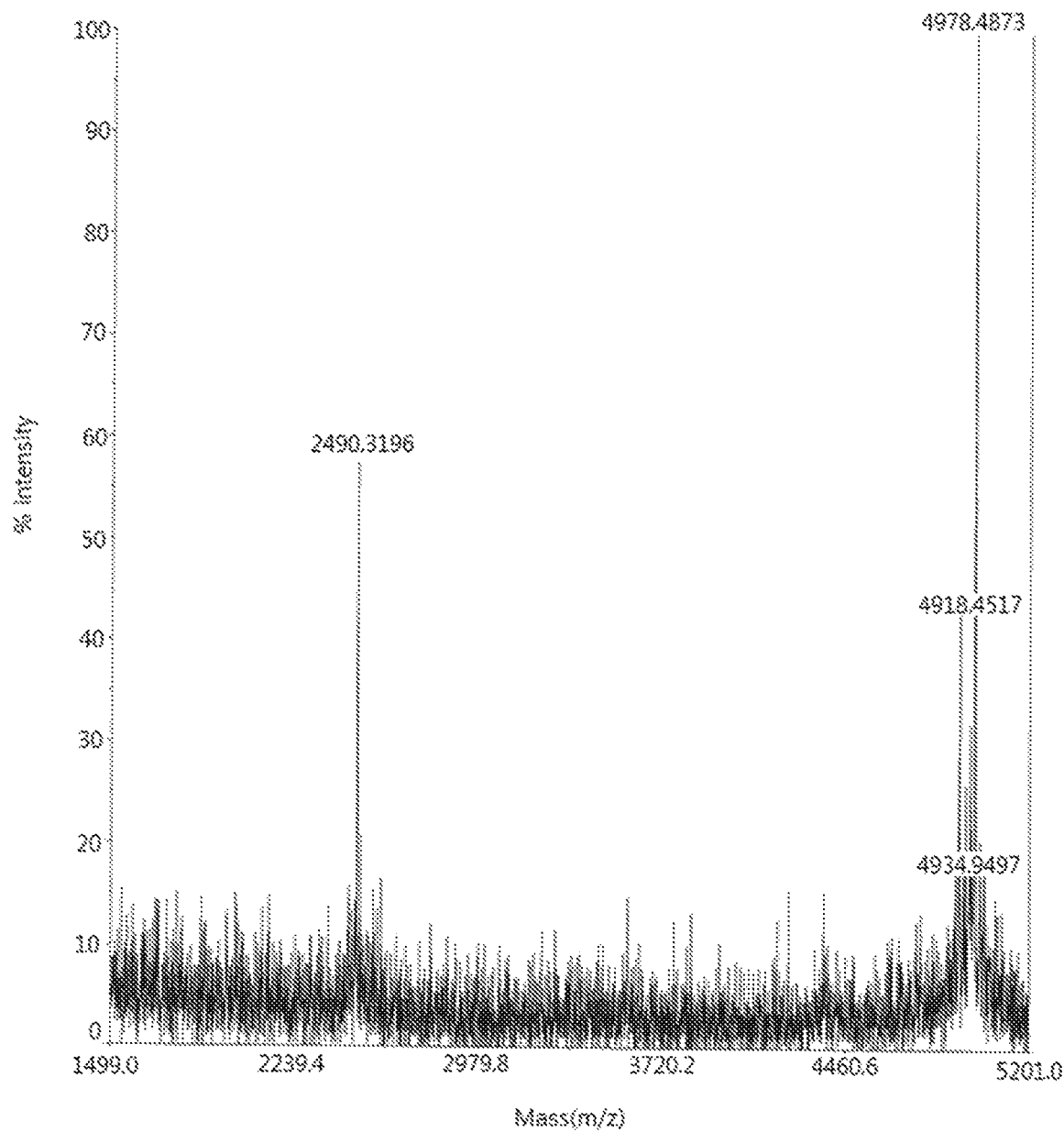
FIG. 2 is a graph showing mass analysis of thymosin β4 sulfoxide.

The ophthalmic preparations prepared in Example 1 and Comparative Examples 1 and 2 and the synthesized thymosin β4 sulfoxide were analyzed by HPLC and LC/MS under the same conditions. The results showed that the retention times and mass analysis values were identical, which confirms that the detected single maximum impurity was thymosin β4 sulfoxide (see FIG. 2).

TABLE 3

| Thymosin β4 (raw material) | | Ex. 1 | | Comp. Ex. 1 | | Comp. Ex. 2 | |
| --- | --- | --- | --- | --- | --- | --- | --- |
| | | | Analysis item | | | | |
| Purity (%) | Single maximum impurity (%) | Purity (%) | Single maximum impurity (%) | Purity (%) | Single maximum impurity (%) | Purity (%) | Single maximum impurity (%) |
| 99.3 | Not detected | 99.1 | 0.29 | 96.3 | 2.9 | 97.9 | 0.7 |

Based on the results in Table 3, it was found that the ophthalmic preparations of the Examples which were prepared under inert gas filling maintained higher purity and had very low amount of impurities compared to those of Comparative Examples 1 and 2, in which an inert gas was excluded during the whole preparation process or a part of the process. Thus, it is found that the ophthalmic preparations of the Examples prepared under nitrogen filling maintain high purity and block the generation of impurities, thereby maintaining a quality similar to the original one.

(3) Storage Stability Test

The ophthalmic preparation prepared in the above Example 1 and Comparative Example 1 and 2 were stored under the condition of 5±3° C. (refrigerating condition) and 25° C., relative humidity (RH) of 40% for 12 months in order to investigate the stability during the storage periods. And the changes in purity and impurity (thymosin β4 sulfoxide) of the ophthalmic preparations were analyzed using the same method of Test Examples (1) and (2). The results are shown in Tables 4 and 5.

Based on the results of Tables 4 and 5, it was found that the ophthalmic preparation of Example 1 which were prepared under an inert gas filling maintained high purity and low amount of the impurity, thymosin β4 sulfoxide, at the initial time after preparation. Further, no significant change of the purity and impurity amount depending on time was observed and therefore the ophthalmic preparation maintained high purity and low impurity amount even after 12 months under the storage conditions of 5±3° C. and 25° C., RH 40%. In particular, under the condition of 5±3° C., the ophthalmic preparation of Example 1 showed high purity of more than 99% and low impurity of less than 1% even after 12 months. In contrast, the ophthalmic preparation of Comparative Examples showed lower purity and higher amount of impurity compared to that of Examples at the initial time after preparation under the conditions of 5±3° C. and 25° C., RH 40%. It was found that the ophthalmic preparation of Comparative Examples shows the decreases of the purity and increase of impurity depending on time. Accordingly, the ophthalmic preparation of Example 1 prepared under inert gas was found to maintain high purity for a long time and block the generation of impurities, thereby exhibiting excellent storage stability.

TABLE 4

| | 5 ± 3° C. (refrigerating conditions) | | | | | |
| --- | --- | --- | --- | --- | --- | --- |
| | Ex. 1 | | Comparative Ex. 1 | | Comparative Ex. 2 | |
| | | | Analysis item | | | |
| | purity (%) | Thymosin β4 sulfoxide (%) | purity (%) | Thymosin β4 sulfoxide (%) | purity (%) | Thymosin β4 sulfoxide (%) |
| Initial value | 99.10 | 0.29 | 96.30 | 2.90 | 97.90 | 0.70 |
| 1 month | 99.43 | 0.57 | 94.76 | 3.30 | 97.20 | 1.20 |
| 2 months | 99.35 | 0.65 | 95.56 | 4.00 | 99.00 | 0.90 |
| 3 months | 99.39 | 0.61 | 91.81 | 5.90 | 99.00 | 0.80 |
| 6 months | 99.28 | 0.72 | 95.18 | 4.00 | 98.10 | 0.90 |
| 9 months | 99.27 | 0.65 | 90.30 | 6.40 | 98.80 | 0.90 |
| 12 months | 99.09 | 0.81 | 94.43 | 3.90 | 98.30 | 0.90 |

TABLE 5

| | 25° C., RH 40% | | | | | |
| --- | --- | --- | --- | --- | --- | --- |
| | Ex. 1 | | Comparative Ex. 1 | | Comparative Ex. 2 | |
| | | | Analysis item | | | |
| | purity (%) | Thymosin β4 sulfoxide (%) | purity (%) | Thymosin β4 sulfoxide (%) | purity (%) | Thymosin β4 sulfoxide (%) |
| Initial value | 99.10 | 0.29 | 96.30 | 2.90 | 97.90 | 0.70 |
| 1 month | 97.76 | 0.77 | 93.60 | 5.40 | 97.70 | 1.30 |
| 2 months | 96.72 | 0.72 | 90.10 | 5.70 | 95.00 | 1.70 |
| 3 months | 95.75 | 0.83 | 87.60 | 5.70 | 93.50 | 1.30 |
| 6 months | 94.38 | 0.99 | 84.70 | 4.50 | 86.30 | 1.60 |
| 9 months | 93.69 | 1.21 | — | — | 81.60 | 2.00 |
| 12 months | 91.98 | 1.32 | — | — | — | — |

The invention claimed is:

1. A method for manufacturing an ophthalmic product comprising thymosin β4 and a container, said method comprising:
 (i) providing a composition comprising (a) a thymosin β4 and (b) an excipient, wherein the composition is prepared by mixing (a) the thymosin β4 and (b) the excipient in the presence of an inert gas;
 (ii) filling the composition comprising the (a) thymosin β4 and the (b) excipient into the container; and
 (iii) sealing the container in the presence of an inert gas to give a sealed container containing the composition comprising the (a) thymosin β4 and the (b) excipient,
 wherein the (b) excipient comprises sodium chloride, potassium chloride, calcium chloride hydrate, magnesium chloride hexahydrate, sodium acetate hydrate, and sodium citrate hydrate,
 wherein the pH of the composition containing the (a) thymosin β4 and the (b) excipient ranges from 6.8 to 7.2, and
 wherein the ophthalmic product maintains at least about 92% purity under the condition of 25° C., 40% Relative Humidity (RH) for 12 months.

2. The method of claim 1, wherein the inert gas of (i) and (iii) is nitrogen or argon.

3. The method of claim 1, wherein the amount of thymosin β4 in the ophthalmic product comprising thymosin β4 ranges from 0.05% (w/v) to 0.5% (w/v).

4. The method of claim 1, wherein the container is selected from the group consisting of a glass container, a polypropylene container, and a low density polyethylene container.

5. The method of claim 1, wherein the pH of the composition comprising the (a) thymosin β4 and the (b) excipient is adjusted by using an acid selected from the group consisting of hydrochloric acid, acetic acid, and phosphoric acid.

6. The method of claim 1, wherein the pH of the composition comprising the (a) thymosin β4 and the (b) excipient is adjusted by using a base selected from the group consisting of sodium hydroxide, potassium hydroxide, and sodium hydrogen carbonate.

7. The method of claim 1, wherein the step (i) further comprises filtering the composition comprising the (a) thymosin β4 and the (b) excipient using a filter.

8. The method of claim 1, further comprising a step of providing the sealed container of the step (iii) into a pouch in the presence of an inert gas.

9. The method of claim 1, wherein the (b) excipient comprises based on 712 g of solvent, 4.89 g of sodium chloride, 573 mg of potassium chloride, 366.72 mg of calcium chloride hydrate, 229 mg of magnesium chloride hexahydrate, 2.98 g of sodium acetate hydrate, and 1.3 g of sodium citrate hydrate.

10. The method of claim 9, wherein the (a) thymosin β4 solution is a aqueous solution of thymosin β4 acetate.

11. The method of claim 1, wherein, in the step (i), the thymosin β4 is mixed with a solvent in the presence of an inert gas while supplying the inert gas at speed of 100 ml/min to 140 ml/min into the solvent thereby removing oxygen dissolved in the solvent.

12. An ophthalmic product prepared by the method of claim 1.

* * * * *

SEQUENCE LISTING

<160> NUMBER OF SEQ ID NOS: 1

<210> SEQ ID NO 1
<211> LENGTH: 43
<212> TYPE: PRT
<213> ORGANISM: Artificial Sequence
<220> FEATURE:
<223> OTHER INFORMATION: thymosine beta 4

<400> SEQUENCE: 1

```
Ser Asp Lys Pro Asp Met Ala Glu Ile Glu Lys Phe Asp Lys Ser Lys
1               5                   10                  15

Leu Lys Lys Thr Glu Thr Gln Glu Lys Asn Pro Leu Pro Ser Lys Glu
            20                  25                  30

Thr Ile Glu Gln Glu Lys Gln Ala Gly Glu Ser
        35                  40
```